United States Patent [19]

Jessel, Jr. et al.

[11] Plant 4,123

[45] Oct. 11, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 712,192

[22] Filed: Aug. 6, 1976

[51] Int. Cl.[2] ..... A01H 5/00

[52] U.S. Cl. ..... Plt./77

[58] Field of Search ..... Plt./77

*Primary Examiner*—Robert E. Bagwill
*Attorney, Agent, or Firm*—Donald D. Jeffery

[57] ABSTRACT

A novel chrysanthemum of spider inflorescence type, having a 9 week response, and the ability to produce quality blooms throughout the year.

3 Drawing Figures

The present invention comprises a new and distinct cultivar of *Chrysanthemum morifolium,* Ramat., hereinafter referred to by the cultivar name Jade (No. 73038052).

Jade is a product of a planned breeding program which had the objective of creating new chrysanthemum cultivars with spider inflorescence type, with white inflorescence color, with 9 week flowering response, and with the ability to produce commercially acceptable quality in year round pot mum programs. Such traits in combinaton were not present in previously available commercial cultivars.

Jade was originated from a cross made in a controlled breeding program in Barberton, Ohio in 1972. The female, or seed parent, was White Spider 2275 (No. 21660E02; unpatented; commercially available), a white spider of parentage unknown to the present inventors. The male, or pollen parent, of Jade was Yellow Daisy Pot (No. 2168AE01; unpatented; commercially available), a yellow spooned daisy sport of White Daisy Pot (No. 21680E01; unpatented; commercially available). White Daisy Pot, a white spooned daisy, is of parentage unknown to the present inventors.

Jade was discovered and selected as one flowering plant within the progeny of the stated cross by Walter H. Jessel, Jr. and William E. Duffett on Mar. 26, 1973 in a controlled environment in Barberton, Ohio.

The first act of asexual reproduction of Jade was accomplished when vegetative cuttings were taken from the initial selection in May, 1973 in a controlled environment in Barberton, Ohio by a technician working under formulations established and supervised by Walter H. Jessel, Jr. and William E. Duffett. Horticultural examination of selected units initiated June 13, 1975 has demonstrated that the combination of characteristics as herein disclosed for Jade are firmly fixed and are retained through successive generations of asexual reproduction.

Jade has not been observed under all possible environmental conditions. The phenotype may vary significantly with variations in environment such as temperature, light intensity, and daylength. The following observations, measurements, and comparisons describe plants grown in Barberton, Ohio under greenhouse conditions which approximate those generally used in commercial practice, as described in Chart A which appears at the end of the present specification. A light intensity chart of general use is shown in ASHAE Trans., Vol. 64, pg. 64 and reference is made thereto.

The following traits have been repeatedly observed and are determined to be basic characteristics of Jade which in combination distinguish this chrysanthemum as a new and distinct cultivar:

1. Flat inflorescence form, reflexing slightly at full maturity.
2. Spider inflorescence type.
3. Ivory white inflorescence color.
4. Diameter across face of inflorescence ranging from 140 to 165 mm. at maturity.
5. Uniform nine week photoperiodic flowering response to short days.
6. Medium plant height (requiring 1 to 2 long day weeks prior to pinch and short days and one application 2500 ppm B-9 SP 14 to 21 days after the beginning of short days to attain a flowered plant height of 30 to 45 cm).
7. Semi-spreading branching pattern.

The accompanying photographic drawings show typical inflorescence and foliage characteristics of Jade with colors being as nearly true as possible with illustrations of this type. Sheet 1 is a color photograph of Jade. Sheet 2 is a black and white photograph showing three views of the inflorescence of Jade. Sheet 3 is a black and white photograph showing the foliage of Jade at three stages of growth.

Of the many commercial cultivars known to the present inventors, the most similar existing cultivar in comparison to Jade is the maternal cultivar, White Spider 2275. Reference is made to attached Chart B which compares certain characteristics of Jade to those same characteristics of White Spider 2275. It will be noted that Jade has smaller diameter across face of inflorescence, shorter plant height, and shorter flowering response period than White Spider 2275. The inflorescence color, inflorescence form and inflorescence type of Jade are similar to those same characteristics of White Spider 2275.

In the following description, color references are made to The Munsell Color Cascade, 1972 edition. The color values were determined between 10:00 and 10:30 A.M. on June 9, 1976 under 200 foot-candle light intensity at Barberton, Ohio.

Botanical classification: *Chrysanthemum morifolium,* Ramat. cv Jade.

INFLORESCENCE

Capitulum (See Sheets 1 and 2 of drawings):

*Form.*—Flat, reflexing slightly with age.

*Type.*—Spider.

*Permanence.*—14 to 18 days.

*Diameter across face.*—140 to 165 mm.

Corolla of ray florets:

*Color (abaxial).*—Approximately 20–15.

*Color (adaxial).*—Approximately 21–15 overlaid with white.

CHART A

AVERAGE GREENHOUSE CHRYSANTHEMUM ENVIRONMENTS USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to 56° F | 65° F to 80° F | 60° F to 75° F | 2 to 4 weeks at 3 Hours Per Night of 7–10 f.c. | To Sept. 15 on - 5:30 PM Off-7:30 AM | From Oct. 15 300 ppm |
| WINTER | 58° F to 62° F | 65° F to 70° F | 60° F to 65° F | 2 to 5 weeks at 5 hours Per Night of 7–10 f.c. | NONE | 300 ppm |
| SPRING | 58° F to 65° F | 65° F to 80° F | 60° F to 75° F | 2 to 4 weeks at 5 Hours Per Night of 7–10 f.c. | From Mar. 15 on - 5:30 PM Off-7:30 AM | To Apr. 15 300 ppm |
| SUMMER | 62° F to 68° F | 70° F to 90° F | 65° F to 75° F | 1 to 2 weeks at 3 Hours Per Night of 7–10 f.c. | on-6:00 PM Off-8:00 AM | NONE |

CHART B

COMPARISON OF JADE AND WHITE SPIDER

| CULTIVAR | INFLORESCENCE COLOR | INFLORESCENCE FORM AND TYPE | DIAMETER ACROSS FACE OF INFLORESCENCE | PLANT HEIGHT | FLOWERING RESPONSE PERIOD |
|---|---|---|---|---|---|
| Jade | Ivory white | Flat spider | 140 to 165 mm | Medium | 9 week |
| White Spider 2275 | Ivory white | Flat spider | 130 to 175 mm | Very tall | 10 week |

COMPARISONS MADE OF PLANTS GROWN IN A GREENHOUSE IN BARBERTON, OHIO UNDER CONDITIONS AS DESCRIBED IN CHART A.

*Persistence.*—Resists shatter.

*Color (abaxial).*—26-4 to white.

*Color (adaxial).*—26-4 to white.

Reproductive organs:

*Androecium.*—Present disc florets only; scant to numerous; scant pollen.

*Gynoecium.*—Present both ray and disc florets.

PLANT

General appearance: semi-spreading branching pattern; medium height.

Foliage (See Sheets 1 and 3):

We claim:

1. A new and distinct cultivar of *Chrysanthemum morifolium,* Ramat. plant known by the cultivar name Jade and particularly characterized as to uniqueness by the combined characteristics of flat inflorescence form, reflexing slightly at full maturity; spider inflorescence type; ivory white inflorescence color; diameter across face of inflorescence ranging from 140 to 165 mm at maturity; uniform 9 week photoperiodic flowering response to short days; medium plant height; and semi-spreading branching pattern.

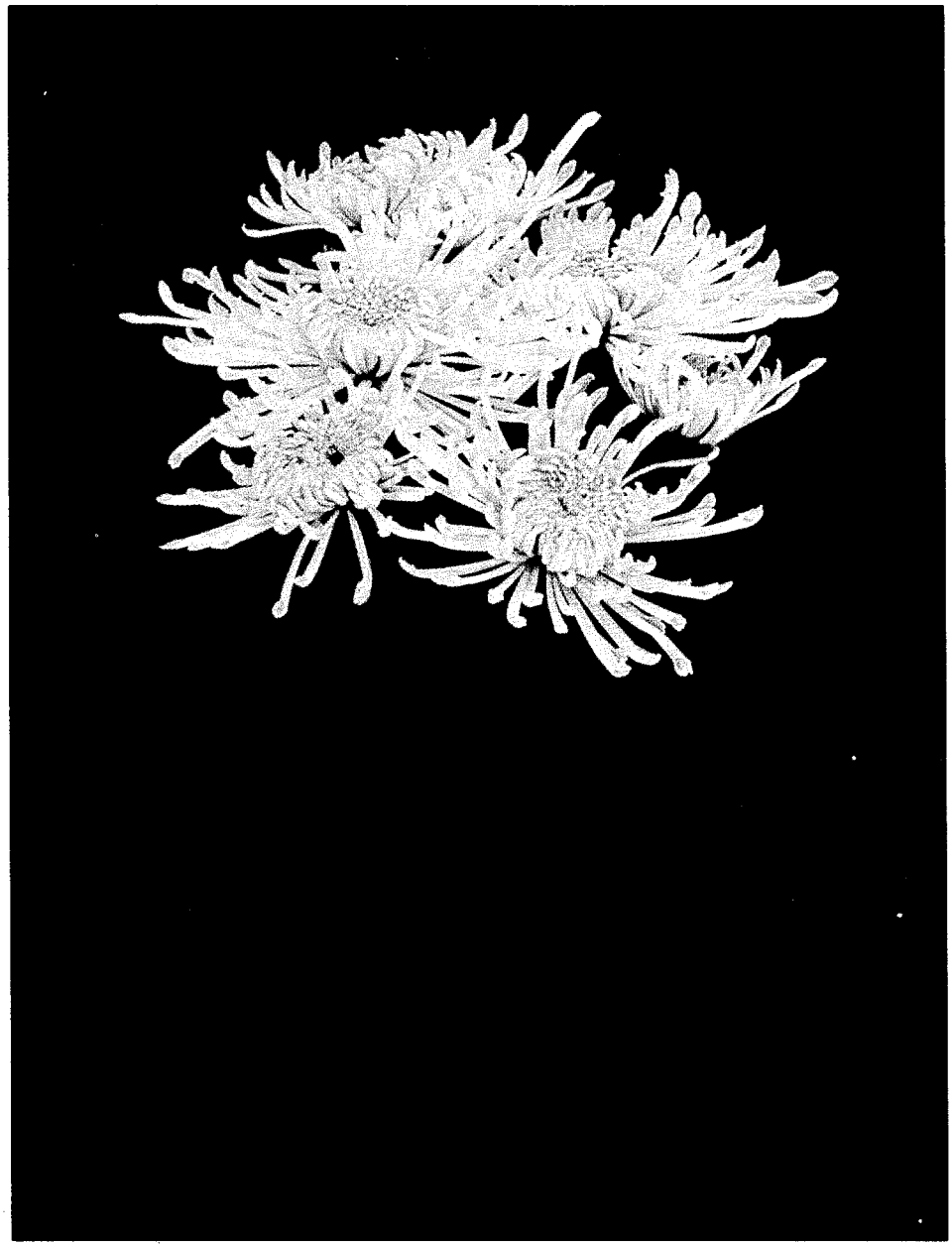

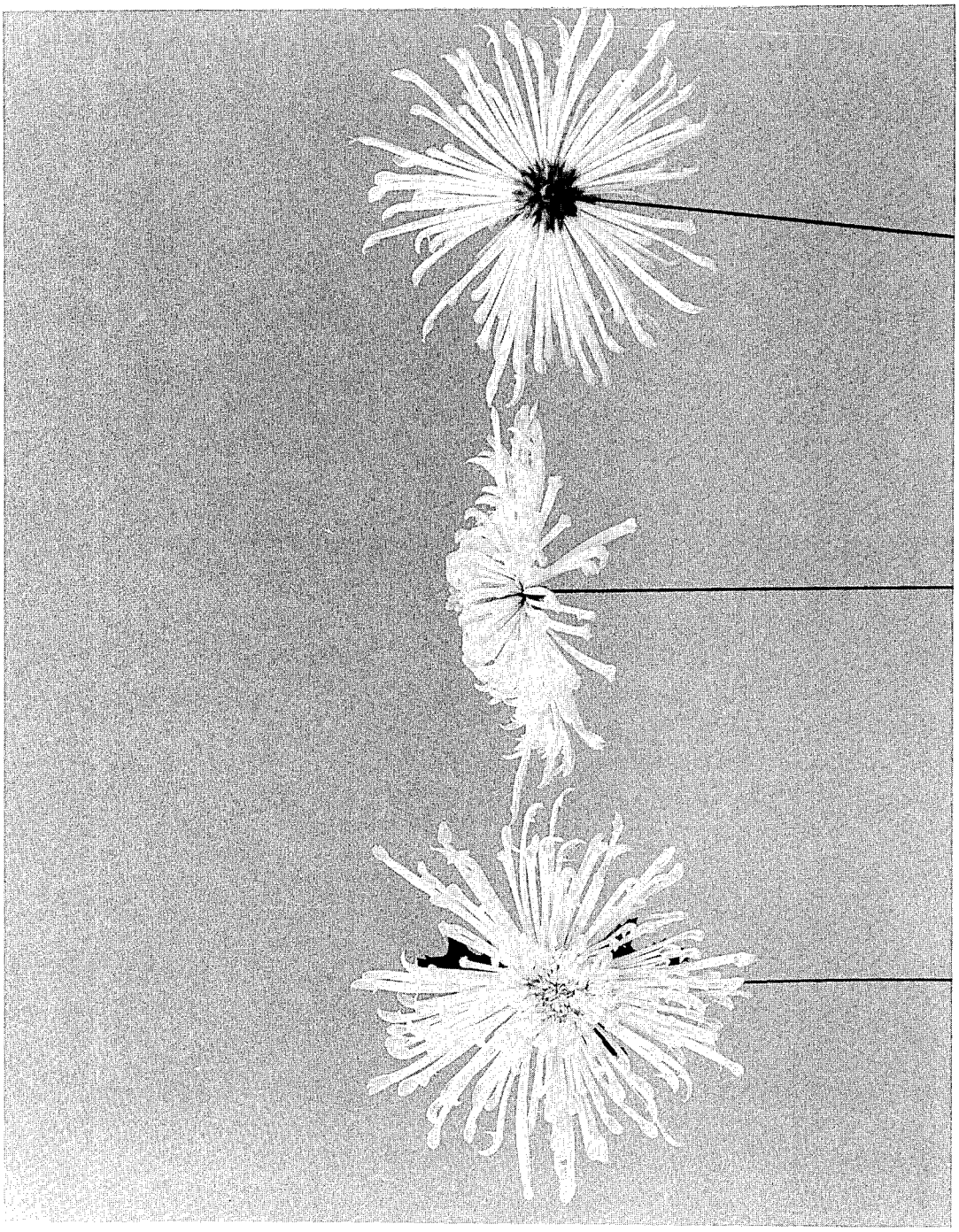

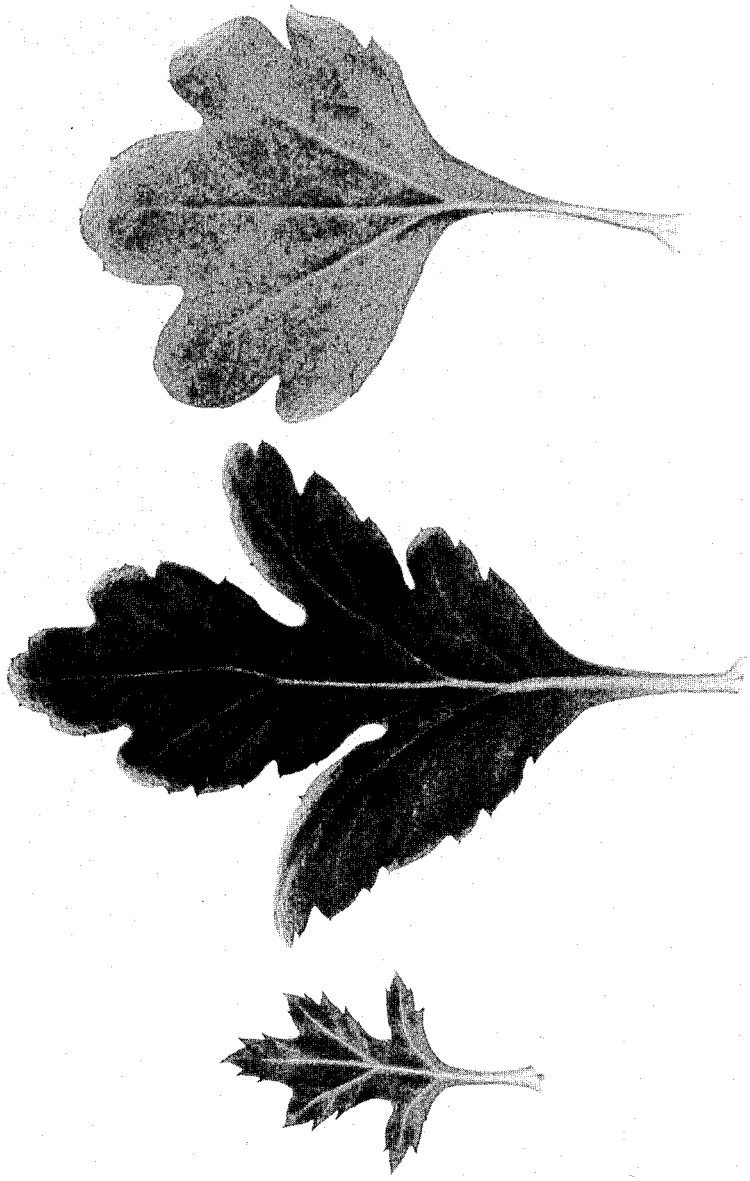

* * * * *